United States Patent
Liu et al.

(10) Patent No.: US 9,421,308 B2
(45) Date of Patent: Aug. 23, 2016

(54) POLYESTER COMPOUNDS SUITABLE FOR HYDROCLAVING

(75) Inventors: Jing Liu, Avon, OH (US); Rahul Bhardwaj, Glen Allen, VA (US)

(73) Assignee: PolyOne Corporation, Avon Lake, OH (US)

( * ) Notice: Subject to any disclaimer, the term of this patent is extended or adjusted under 35 U.S.C. 154(b) by 275 days.

(21) Appl. No.: 14/000,726

(22) PCT Filed: Feb. 21, 2012

(86) PCT No.: PCT/US2012/025948
§ 371 (c)(1),
(2), (4) Date: Aug. 21, 2013

(87) PCT Pub. No.: WO2012/115971
PCT Pub. Date: Aug. 30, 2012

(65) Prior Publication Data
US 2013/0323121 A1    Dec. 5, 2013

Related U.S. Application Data

(60) Provisional application No. 61/445,421, filed on Feb. 22, 2011.

(51) Int. Cl.
 C08L 25/00 (2006.01)
 C08L 67/03 (2006.01)
 C08L 81/06 (2006.01)
 A61L 31/04 (2006.01)
 C08L 67/02 (2006.01)

(52) U.S. Cl.
 CPC .............. *A61L 31/041* (2013.01); *C08L 67/02* (2013.01); *C08L 81/06* (2013.01)

(58) Field of Classification Search
None
See application file for complete search history.

(56) References Cited

U.S. PATENT DOCUMENTS

| | | |
|---|---|---|
| 2006/0287489 A1 | 12/2006 | Crawford et al. |
| 2008/0000917 A1 | 1/2008 | Agarwal et al. |
| 2008/0119631 A1 | 5/2008 | Mullen |
| 2008/0293882 A1 | 11/2008 | Germroth et al. |
| 2009/0093573 A1 | 4/2009 | Germroth et al. |
| 2009/0093574 A1 | 4/2009 | Crawford et al. |

*Primary Examiner* — Ana Woodward
(74) *Attorney, Agent, or Firm* — John H. Hornickel

(57) ABSTRACT

A compound suitable for hydroclaving is disclosed, comprising polyester, polysulfone, and an epoxy-functional styrene-acrylate oligomer. In order for successful repetitious hydroclaving to be possible, the compound must also have a polysulfone content of greater than 45 weight percent of the compound.

14 Claims, No Drawings

POLYESTER COMPOUNDS SUITABLE FOR HYDROCLAVING

CLAIM OF PRIORITY

This application claims priority from U.S. Provisional Patent Application Ser. No. 61/445,421 filed on Feb. 22, 2011, which is incorporated by reference.

FIELD OF THE INVENTION

This invention relates to polyester compounds which can endure hydroclaving necessary for proper sterilization in health care uses.

BACKGROUND OF THE INVENTION

In the past few years, a new type of polyester compound has become commercially available from Eastman Chemical Company of Kingsport, Tenn. bearing the Tritan™ brand. A very large number of patent applications have been filed and published concerning this impressive technology.

Among the many applications published thus far, several have attempted to address the need for compounds containing Tritan™ brand polyester resins to have stability at high temperatures or a high glass transition temperature or other indications that the new polyester resin itself needs compounding assistance to make the polyester compound more tolerant of high operational temperatures. Three examples of such patent publications are US2008/0293882 (Germroth et al.); US2009/0093573 (Germroth et al.); and US 2009/0093574 (Crawford et al.)

To be useful in the health care industry, thermoplastic articles need to be durable enough to withstand repeated events of steam sterilization in a hydroclave.

SUMMARY OF THE INVENTION

What the art needs is a hydroclavable polyester compound suitable for use in the health care industry.

The present invention solves this problem by formulating a polyester compound from Tritan™ brand polyester, polysulfone, and an epoxy-functional styrene-acrylate oligomer.

The present invention differs from the patent portfolio of Eastman Chemical Company in respect of its Tritan™ brand polyester resin and compounds in that an epoxy-functional styrene-acrylate oligomer has been found to be necessary for plastic articles made from the compound to achieve acceptable hydroclavable properties.

Unexpectedly, moreover, it has been found that a significant inflection point exists in acceptable hydroclavable properties depending upon the weight percent of polysulfone in the compound used to form the plastic article.

EMBODIMENTS OF THE INVENTION

Polyester

The compound of the present invention uses commercially available grades of Tritan™ brand polyester. Among the many available grades, non-limiting examples of suitable grades include TX1000, TX2000, TX1001, TX2001, TX1500HF, TX1501HF, or combinations thereof. These proprietary polyesters are well known and accepted in the market as a new polymer for use in plastic articles previously made from polycarbonate. Unlike polycarbonate, polymerization of these polyesters do not involve the use of bisphenol-A.

In its broadest articulation of these commercial polyesters, as explained in US 2006/0287482 A1 (Crawford et al.), incorporated by reference herein, the polyester can be a composition comprising at least one polyester which comprises: (a) a dicarboxylic acid component comprising: i) 70 to 100 mole % of terephthalic acid residues; ii) 0 to 30 mole % of aromatic dicarboxylic acid residues having up to 20 carbon atoms; and Iii) 0 to 10 mole % of aliphatic dicarboxylic acid residues having up to 16 carbon atoms; and (b) a glycol component comprising: i) 1 to 99 mole % of 2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of said polyester is from 0.35 to less than 0.70 dL/g as determined in 60/40 (wt/wt) phenol/tetrachloroethane at a concentration of 0.5 g/100 ml at 25° C.; and wherein said polyester has a Tg from 110 to 200° C.

As also explained in US 2006/0287494 A1 (Crawford et al.), incorporated by reference herein, the polyester can be a composition comprising at least one polyester which comprises: (a) a dicarboxylic acid component comprising: i) 70 to 100 mole % of terephthalic acid residues; ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising: i) greater than 81 to 99 mole % of 2,2,4,4-tetramethyl-1,3-cyclobutanediol residues; and ii) less than 19 to 1 mole % of 1,4-cyclohexanedimethanol residues, wherein the total mole % of the dicarboxylic acid component is 100 mole %, and the total mole % of the glycol component is 100 mole %; and wherein the inherent viscosity of said polyester is from 0.10 to 1.2 dL/g as determined in 60/40 (wt/wt) phenol/tetrachloroethane at a concentration of 0.5 g/100 ml at 25° C.; and wherein said polyester has a Tg from 135 to 200° C.

Other explanations of the Tritan™ brand polyester useful in the present invention are found in US 2008/0293882 (Germroth et al.); US 2009/0093573 (Germroth et al.); and US 2009/0093574 (Crawford et al.), all of which are incorporated by reference herein.

Polysulfone

Polysulfone is one of the highest performing amorphous engineering thermoplastic polymers known. Its high hydrolysis stability makes it a candidate for use in hydroclaving. It has a tensile strength at yield at 23° C. of 70-76 MPa, an elongation at break of 10-80%, a tensile modulus at 23° C. of 1.5-2.7 GPa, a long term service temperature range of 150° C.-180° C., and a heat deflection temperature at 1.8 MPa of 160° C.-174° C.

The repeating unit for polysulfone is shown in Formula I below.

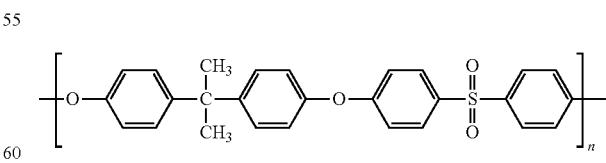

I

Polysulfone is commercially available from any number of sources, including Sabic Innovative Plastics and Solvay Advanced Polymers of Alpharetta, Ga. Of the various manufacturers and grades, Udel™ P-3703 polysulfone from Solvay is presently preferred because it is resistant to oxidation and hydrolysis and withstands prolonged exposure to high temperatures and repeated sterilization and is highly resistant to mineral acids, alkali and salt solutions.

Epoxy-Functional Styrene-Acrylate Oligomer

Unexpectedly, blends of Tritan™ brand polyester and polysulfone require an epoxy-functional styrene-acrylate oligomer in order to have acceptable hydroclaving properties. The currently preferred epoxy-functional styrene-acrylate oligomer Joncryl™ brand chain extender marketed by BASF Corporation.

Additional information about the epoxy functional low molecular weight styrene-acrylate copolymer is disclosed in U.S. Pat. No. 6,605,681 (Villalobos et al.) and U.S. Pat. No. 6,984,694 (Blasius et al.), incorporated by reference herein.

Stated another way using those patents for reference, the oligomeric chain extender is the polymerization product of (i) at least one epoxy-functional (meth)acrylic monomer; and (ii) at least one styrenic and/or (meth)acrylic monomer, wherein the polymerization product has an epoxy equivalent weight of from about 180 to about 2800, a number-average epoxy functionality (Efn) value of less than about 30, a weight-average epoxy functionality (Efw) value of up to about 140, and a number-average molecular weight (Mn) value of less than 6000. Preferably, the oligomeric chain extender a polydispersity index of from about 1.5 to about 5.

Various Joncryl™ grades available and useful from BASF are ADR-4300, ADR-4370-S, ADR-4368-F, and ADR-4368-C, which are all solids. Alternatively, one can use liquid grades, namely: ADR-4380, ADR-4385, and ADR-4318.

Particularly preferred is Joncryl™ ADR-4368-CS. The number average molecular weight of this grade is less than 3000 with approximately more than 4 epoxy functionalities per polymer chain.

Formula II shows the epoxy-functional styrene-acrylate polymer, wherein $R_1$-$R_5$ can be H, $CH_3$, a higher alkyl group having from 2 to 10 carbon atoms, or combinations thereof; and $R_6$ can be an alkyl group; and wherein x, y, and z each can be between 1 and 20.

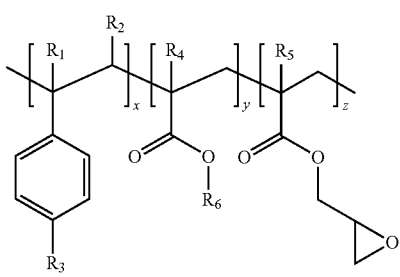

II

Optional Additives

The compound of the present invention can include conventional plastics additives in an amount that is sufficient to obtain a desired processing or performance property for the compound. The amount should not be wasteful of the additive nor detrimental to the processing or performance of the compound. Those skilled in the art of thermoplastics compounding, without undue experimentation but with reference to such treatises as *Plastics Additives Database* (2004) from Plastics Design Library (www.williamandrew.com), can select from many different types of additives for inclusion into the compounds of the present invention.

Non-limiting examples of optional additives include adhesion promoters; biocides (antibacterials, fungicides, and mildewcides), anti-fogging agents; anti-static agents; bonding, blowing and foaming agents; dispersants; fillers and extenders; fire and flame retardants and smoke suppressants; impact modifiers; initiators; lubricants; micas; pigments, colorants and dyes; plasticizers; processing aids; release agents; silanes, titanates and zirconates; slip and anti-blocking agents; stabilizers; stearates; ultraviolet light absorbers; viscosity regulators; waxes; and combinations of them.

Table 1 shows the acceptable, desirable, and preferable ranges of ingredients for the polymer compound of the present invention. The compound can comprise, consist essentially, or consist of the following ingredients. The ranges expressed include all integers within that range. The selection for each ingredient can be made from each category interchangeably, such that an acceptable range of one ingredient can be used with a desirable range of another ingredient, etc.

TABLE 1

Ranges of Ingredients for Hydroclavable Polyester Compound

| Ingredient (Wt. Percent) | Acceptable | Desirable | Preferable |
|---|---|---|---|
| Polyester | 18-49 | 23-44 | 29-39 |
| Polysulfone | 50-80 | 55-75 | 60-70 |
| Epoxy-Functional Styrene-Acrylate Oligomer | 0.5-2 | 0.5-2 | 0.8-1.2 |
| Optional Additives | 0-10 | 0-5 | 0-1 |

Processing

The preparation of compounds of the present invention is uncomplicated. The compound of the present can be made in batch or continuous operations.

Mixing in a continuous process typically occurs in an extruder that is elevated to a temperature that is sufficient to melt the polymer matrix with addition either at the head of the extruder or downstream in the extruder of the solid ingredient additives. Extruder speeds can range from about 50 to about 500 revolutions per minute (rpm), and preferably from about 200 to about 300 rpm. Typically, the output from the extruder is pelletized for later extrusion or molding into polymeric articles.

Mixing in a batch process typically occurs in a Banbury mixer that is also elevated to a temperature that is sufficient to melt the polymer matrix to permit addition of the solid ingredient additives. The mixing speeds range from 60 to 1000 rpm. Also, the output from the mixer is chopped into smaller sizes for later extrusion or molding into polymeric articles.

Subsequent extrusion or molding techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (www.williamandrew.com), one can make articles of any conceivable shape and appearance using compounds of the present invention.

USEFULNESS OF THE INVENTION

Compounds of the present invention are useful for molding into plastic articles which must be subjected to repeated steam sterilization by hydroclaving.

A hydroclave is used in the medical and healthcare industry for the sterilization of containers, implements, tools, and other objects which are not disposable but require sterilization between each use. Infectious disease is continuously a threat to any medical or other healthcare facility. Sterilization against infectious agents is a necessity. The hydroclave provides steam-based sterilization of the plastic articles made from compounds of the present invention.

For purposes of this invention, the hydroclave employed to qualify the inventive compounds was the Harvey MC10 Hydroclave. As explained by its manufacturer, GETINGE/Castle of Rancho Dominguez, Calif., this hydroclave is a fully-automated, microprocessor-controlled autoclave with a 10-inch diameter by 15½-inch deep, round, stainless steel chamber and a nonrecirculating water system. This system utilizes fresh water for each sterilization cycle and the used water is exhausted directly into a sink/drain or into the optional non-recirculating water collection reservoir. The autoclave operates at 115 volts ±5% or 230 volts ±5%, 50/60 Hz with a loading of 1.495 kW. The unit requires a 20 amp circuit breaker. The microprocessor-controlled sterilization parameters are constantly monitored to assure proper sterilization for each programmed cycle. A time-temperature interlock assures that the sterilization cycle does not begin until the correct parameters are met. The sterilizer is UL and IEC 601-1 listed and is certified by ETL, CSA, ASME, and ANSI/ADA.

Embodiments of the invention are further explained by the following examples.

EXAMPLES

Table 2 shows the formulations for Comparative Examples A-C and Examples 1-2, the extrusion and molding conditions and physical test results.

TABLE 2

| Ingredient | Source | A | 1 | 2 | B | C |
|---|---|---|---|---|---|---|
| Tritan TX2000 Polyester | Eastman Chemical | 50.000 | 40.000 | 40.000 | 40.000 | 40.000 |
| POLYSULFONE P-3703 NAT | Solvay | 39.800 | 48.800 | 53.800 | 49.800 | 54.800 |
| Irganox 1010 Stabilizer | BASF | 0.200 | 0.200 | 0.200 | 0.200 | 0.200 |
| PARALOID KM334 Impact Modifier | Dow Chemical | 10.000 | 10.000 | 5.000 | 10.000 | 5.000 |
| Joncryl ADR 4368 Oligomer | BASF | | 1.000 | 1.000 | | |
| Total | | 100.000 | 100.000 | 100.000 | 100.000 | 100.000 |
| WP 25 mm twin screw extruder | | | | | | |
| Dried Tritan TX2000 Polyester Resin for four hours at 86.6° C. and Dried Polysulfone for three hours at 148.8° C., to achieve moisture content below 0.02 wt. %: | | Yes | Yes | Yes | Yes | Yes |
| Zone 1 (° C.) | | 276.7 | 276.7 | 276.7 | 276.7 | 276.7 |
| Zone 2 (° C.) | | 276.7 | 276.7 | 276.7 | 276.7 | 276.7 |
| Zone 3 (° C.) | | 282.2 | 282.2 | 282.2 | 282.2 | 282.2 |
| Zone 4 (° C.) | | 282.2 | 282.2 | 282.2 | 282.2 | 282.2 |
| Zone 5 (° C.) | | 287.8 | 287.8 | 287.8 | 287.8 | 287.8 |
| Zone 6 (° C.) | | 287.8 | 287.8 | 287.8 | 287.8 | 287.8 |
| Zone 7 (° C.) | | 287.8 | 287.8 | 287.8 | 287.8 | 287.8 |
| Zone 8 (° C.) | | 293.3 | 293.3 | 293.3 | 293.3 | 293.3 |
| Die Temp (° C.) | | 276.7 | 276.7 | 276.7 | 276.7 | 276.7 |
| RPM/Side screw RPM | | 250 | 250 | 250 | 250 | 250 |
| % Torque | | 57 | 65 | 65 | 57 | 58 |
| Die Press | | 231 | 286 | 267 | 232 | 239 |
| Melt Temp (° C.) | | 292 | 291 | 290 | 289 | 289 |
| Melt Temp Pyro (° C.) | | 315.6 | 600 | 600 | 600 | 600 |
| 88 Nissei Molding Machine Drying Conditions: | | | | | | |
| Temperature | | 90° C. | 90° C. | 90° C. | 90° C. | 90° C. |
| MOISTURE | | 0.01% | 0.01% | 0.01% | 0.01% | 0.01% |
| Temperatures: | | | | | | |
| Zone 1 (Nozzle) | | 550 | 550 | 550 | 550 | 550 |
| Zone 2 | | 540 | 540 | 540 | 540 | 540 |
| Zone 3 | | 530 | 530 | 530 | 530 | 530 |
| Zone 4 | | 530 | 530 | 530 | 530 | 530 |
| Mold | | 200 | 200 | 200 | 200 | 200 |
| Oil Temp | | 90 | 90 | 90 | 90 | 90 |
| Speeds: | | | | | | |
| Screw RPM | | 60-122 | 60-122 | 60-122 | 60-122 | 60-122 |
| SM - Inj Vel 1 | | 54-50% | 54-50% | 54-50% | 54-50% | 54-50% |
| S1 - Inj Vel 2 | | 46-40% | 46-40% | 46-40% | 46-40% | 46-40% |
| S2 - Inj Vel 3 | | 38-30% | 38-30% | 38-30% | 38-30% | 38-30% |
| S3 - Inj Vel 4 | | 30-20% | 30-20% | 30-20% | 30-20% | 30-20% |
| S4 - Inj Vel 5 | | 22-15% | 22-15% | 22-15% | 22-15% | 22-15% |

TABLE 2-continued

|  |  | A | 1 | 2 | B | C |
|---|---|---|---|---|---|---|
| Pressures: Inj Press Stg - Time (sec) | | | | | | |
| Injection Pressure 1 | | 99% | 99% | 99% | 99% | 99% |
| Hold Pressure 2 | | 24% | 24% | 24% | 24% | 24% |
| Hold Pressure 3 | | 18% | 18% | 18% | 18% | 18% |
| Back Pressure | | 1% | 1% | 1% | 1% | 1% |
| Timers: | | | | | | |
| Injection Hold (sec) | | 7 | 7 | 7 | 7 | 7 |
| Cure Time (sec) | | 20 | 20 | 20 | 20 | 20 |
| Operation Settings: | | | | | | |
| Shot Size (SM) | | 54 | 54 | 54 | 54 | 54 |
| Cushion | | 11 | 11 | 11 | 11 | 11 |
| Cut-Off Position | | 14 | 14 | 14 | 14 | 14 |
| Cut-Off Pressure | | 2000 | 2000 | 2000 | 2000 | 2000 |
| Cut-Off Time | | N/A | N/A | N/A | N/A | N/A |
| Cut-Off Mode | | POS | POS | POS | POS | POS |
| Decompression | | 6 | 6 | 6 | 6 | 6 |
| TEST | TEST METHOD | | | | | |
| Specific Gravity | ASTM D-792 | 1.1925 | 1.1975 | 1.2045 | 1.1975 | 1.2045 |
| Ultimate Tensile @ yield (psi) - 2.0 in/min | ASTM D-638 (Rigid) | 7260 | 7860 | 8550 | 7860 | 8370 |
| Tensile @ Break - 2.0 in/min | ASTM D-638 (Rigid) | 6690 | 6762 | 6753 | 7846 | 8128 |
| Tensile Modulus (psi) - 2.0 in/min | ASTM D-638 | 205956 | 216806 | 228124 | 211905 | 225194 |
| Elongation @ Break - 2.0 in/min | ASTM D-638 | 85 | 81 | 61 | 120 | 120 |
| Flexural Modulus (psi) - 0.5 in/min | ASTM D-790 | 270000 | 285000 | 30600 | 279000 | 30100 |
| Flexural Yield (psi) - 0.5 in/min | ASTM D-790 | 11600 | 12420 | 13480 | 12310 | 13330 |
| HDT @ 66 PSI | ASTM D-648 | 121.85 | 154.35 | 157.75 | 136.1 | 146.1 |
| Izod, 1/8" (3.57 mm) RT | ASTM D-256 | 3.226 | 3.731 | 2.934 | 1.851 | 1.532 |

A comparison of Comparative Example B and Example 1 shows that the addition of oligomer did not alter the physical properties of an impact modified version of the compounds of the invention, except with respect to HDT which was improved by the presence of the oligomer and Elongation which decreased because of the presence of the oligomer.

A comparison of Comparative Example C and Example 2 shows the same comparative results as found between Comparative Example B and Example 1.

A comparison of Examples 1 and 2 shows that twice as much impact modifier present improves flexibility and elongation. However, other experiments showed that adding too much impact modifier will cause a loss of hydroclavability. It was found that adding not more than two weight percent of impact modifier did not adversely affect hydroclavability.

Table 3 shows the formulations for Comparative Examples D-M and Examples 3-4. Table 4 shows extrusion conditions for Comparative Examples D-M and Examples 3-4 to prepare pellets of the compounds tested and also shows the molding conditions to prepare ASTM test bars for hydroclaving. Table 3 also shows the hydroclaving test results.

Hydroclave testing used the Harvey MC10 Hydroclave described above. Each cycle required 18 minutes to heat up the hydroclave chamber to 135° C. The chamber was then maintained for another 18 minutes at 135° C. and 248 kPa (36 PSI) of steam pressure. The chamber was then allowed to cool down for 10 minutes with the door to the chamber closed, followed by an additional 10 minutes with the door to the chamber open. Solvay as a maker of polysulfone has published this test method on the "Sulfone Polymers Performance Data" web page and the "Sterilization" tab, as of the date of this document located at http://www.solvayplastics.com/sites/solvayplastics/EN/Companies/solvav_advanced_polymers/solvayapproducts/SulfonePolymers/Pages/Overview.aspx For each cycle, about 20 ASTM tensile test bars prepared according to the molding conditions shown in Table 4 were placed in the hydroclave chamber. Because of the small volume of the chamber and the number of test bars to be tested, most of the test bars were in contact with other test bars during the hydroclave cycle.

From this physical arrangement of test bars in the chamber came the unexpected discovery that the hydroclave cycle may not have caused deformation of the test bars but did generate a surface stickiness which cohesively bonded the bars of the Comparative Examples together, either in the first cycle or by the fifth cycle. For some pairs of test bars in contact, the amount of surface stickiness caused varying amounts of hand pressure to peel one bar away from another.

Upon discovery of this phenomenon, each Comparative Example D-M and Examples 3 and 4 was evaluated for deformation or stickiness.

TABLE 3

| | D | E | F | G | H | I | J | K | L | M | 3 | 4 |
|---|---|---|---|---|---|---|---|---|---|---|---|---|
| Tritan TX2000 Polyester | 100 | | 39.8 | 49.8 | 59.8 | 78.8 | 68.8 | 63.8 | 58.8 | 53.8 | 48.8 | 38.8 |
| POLYSULFONE P-3703 NAT | | 100 | 60.0 | 50.0 | 40.0 | 20.0 | 30.0 | 35.0 | 40.0 | 45.0 | 50.0 | 60.0 |
| Irganox 1010 Stabilizer | | | 0.2 | 0.2 | 0.2 | 0.2 | 0.2 | 0.2 | 0.2 | 0.2 | 0.2 | 0.2 |
| Joncryl ADR 4368 Oligomer | | | | | | 1.0 | 1.0 | 1.0 | 1.0 | 1.0 | 1.0 | 1.0 |
| Total | 100 | 100 | 100.0 | 100.0 | 100.0 | 100.0 | 100.0 | 100.0 | 100.0 | 100.0 | 100.0 | 100.0 |
| Hydroclave Test | | | | | | | | | | | | |
| One Cycle | Def | | OK | OK | OK | | | | | | | |
| Five Cycles | | | Def | Def | Def | VS | VS | VS | VS | SS | SS | VSS |
| 35 Cycles | | | | | | | | | | | OK | OK |
| 100 Cycles | | OK | | | | | | | | | | OK |

Def = Deformed
VS = Very Sticky
SS = Slightly Sticky
OK = Not Sticky

TABLE 4

| | D-M, 3, 4 |
|---|---|
| WP 25 mm twin screw extruder | |
| Polymers Dried as in Table 2 | Yes |
| Zone 1 (C.) | 276.7 |
| Zone 2 (C.) | 276.7 |
| Zone 3 (C.) | 282.2 |
| Zone 4 (C.) | 282.2 |
| Zone 5 (C.) | 287.8 |
| Zone 6 (C.) | 287.8 |
| Zone 7 (C.) | 287.8 |
| Zone 8 (C.) | 293.3 |
| Zone 9 (C.) | x |
| Adapter Temp (C.) | x |
| Die Temp (C.) | 293.3 |
| RPM/Side screw RPM | 250.0 |
| % Torque | Variable (57~65) |
| Die Press | Variable (231~286) |
| Melt Temp (° C.) | Variable (289-292) |
| Melt Temp Pyro (° C.) | 315.6 |
| 88 Nissei Molding Machine | |
| Drying Conditions: | |
| Temperature | 90 |
| MOISTURE | 0.01% |
| Temperatures: | |
| Zone 1 (Nozzle) | 287.8 |
| Zone 2 | 282.2 |
| Zone 3 | 276.7 |
| Zone 4 | 276.7 |
| Mold | 93.3 |
| Oil Temp | 32.2 |
| Speeds: | |
| Screw RPM | 60%-121 |
| SM - Inj Vel 1 | 52-50% |
| S1 - Inj Vel 2 | 42-40% |
| S2 - Inj Vel 3 | 34-30% |
| S3 - Inj Vel 4 | 26-20% |
| S4 - Inj Vel 5 | 18-15% |
| Pressures: | |
| Inj Press Stg - Time (sec) | |
| Injection Pressure 1 | 90% |
| Hold Pressure 2 | 26% |
| Hold Pressure 3 | 20% |
| Back Pressure | 1% |
| Timers: | |
| Injection Hold (sec) | 7 |
| Cure Time (sec) | 25 |
| Operation Settings: | |
| Shot Size (SM) | 52 |
| Cushion | 14 |
| Cut-Off Position | 10 |
| Cut-Off Pressure | 2000 |
| Cut-Off Time | n/a |
| Cut-Off Mode | pos |
| Decompression | 8 |

The hydroclave cycle test results showed, as expected, that Comparative Example D (100% polyester) deformed after one hydroclave cycle while Comparative Example E (100% polysulfone) endured 100 hydroclave cycles excellently.

Unexpectedly, Comparative Examples F-H tolerated one hydroclave cycle but deformed by five hydroclave cycles. Only repetitious testing had uncovered those observations, regardless of the concentrations of polyester and polysulfone in the compound. These Comparative Examples F-H demonstrated that the presence of the oligomer was required for compounds of the invention to perform successfully during repeated hydroclave cycles.

Even more unexpectedly, the performance of Comparative Examples I-M and Examples 3 and 4 showed that compounds with the same amount of oligomer added were affected by the cohesive stickiness described above depending upon the concentration of polysulfone in the compound. Most unexpectedly, the performance of those Comparative Examples I-L (polysulfone content in the range of 20-40 weight percent) were utter failures because of extreme stickiness and cohesive bonding within the first five hydroclave cycles. During the testing from the first cycle to the fifth cycle, it is true that the amount of stickiness decreased. But by the fifth cycle, the test bars remained very sticky and unacceptable for use in the medical or healthcare industries. No one would want a plastic article to be incapable of even 5 cycles without overcoming this phenomenon of surface stickiness and cohesive bonding requiring hand pressure to peel apart two plastic articles.

Only after the polysulfone content reached 45 weight percent or more (Comparative Example M and Examples 3 and 4) did it become easy to physically separate contiguous test bars from the cohesive bonding formed by the surface stickiness between those test bars.

Therefore, there was found to be an inflection point of acceptable performance between compounds having 45 weight percent of polysulfone and compounds having 50 weight percent of polysulfone, in respect of surface stickiness after repeated hydroclave cycles. Compounds of the invention with greater than 45 weight percent, and especially at least 50 weight percent, of polysulfone were found to be acceptable for use in hydroclaving, because as shown in Table 3, the hydroclave test is OK up to at least 35 cycles.

Compounds having between 50 and 60 weight percent, i.e., each weight percent of polysulfone between 50 and 60 as if numerically repeated here, were considered to be even more desirable as hydroclavable compounds of the invention. Compounds having at least 60 weight percent of polysulfone were selected as preferred, including each weight percent of polysulfone up to an amount of polysulfone such as 70 weight percent at which point cost of polysulfone becomes relevant as compared with a pure polysulfone article.

Table 5 shows the physical properties of preferred Example 4 and Comparative Example E (100% polysulfone) over the course of 100 hydroclave cycles.

TABLE 5

| Hydroclave Cycles | Example 4 | | | | | | Comparative Example E | | |
|---|---|---|---|---|---|---|---|---|---|
| | 0 | 1 | 5 | 25 | 50 | 100 | 0 | 50 | 100 |
| Ultimate Tensile (psi) | 9340 | 9600 | 9620 | 10300 | 10600 | 9920 | 11300 | 13300 | 12700 |
| Tensile @ Break | 7039 | 6949 | 6637 | 6360 | 7305 | 9920 | 9489 | 11890 | 12650 |
| Tensile Modulus (psi) | 251982 | 231886 | 240976 | 260958 | 264212 | 254592 | 283514 | 304000 | 282178 |
| Elongation @ Break | 66 | 61 | 58 | 19 | 8 | 5 | 130 | 7 | 6 |
| Flexural Modulus (psi) | 347000 | 338000 | 345000 | 345000 | 359000 | 380000 | 390000 | 417000 | 447000 |
| Flexural Yield (psi) | 15200 | 15300 | 15540 | 16020 | 16590 | 17400 | 18150 | 18990 | 19760 |
| HDT @ 66 PSI | 168 | 165 | 163 | 169 | 170 | 172 | 177 | 177 | 179 |
| Izod, ⅛" (3.57 mm) RT | 0.93 | 0.81 | 0.97 | 0.78 | 0.68 | 0.54 | 1.12 | 0.87 | 0.77 |

Table 5 demonstrated that compounds of the invention, a blend of Tritan™ polyester and polysulfone and epoxy-functional styrene-acrylate oligomer match with pure polysulfone in terms of hydroclavability. Not only were the properties similar, but also the progression of physical property measurements through the number of hydroclave cycles showed relatively constant properties, except for elongation at break. But in that respect, Example 4 performed no worse than Comparative Example E.

Any number of medical or healthcare devices requiring repeated hydroclaving is now capable of being made using the compounds of the invention, particularly as a replacement for expensive polysulfone plastic articles.

From these Comparative Examples and Examples, it was found that:

(a) the epoxy-functional styrene-acrylate oligomer is a required ingredient for compounds of the invention to perform in successive hydroclave cycles, and (b) compounds of the invention can only withstand successive hydroclave cycles, even with the oligomer present, when the weight percent of the polysulfone in the compound is greater than 45 percent and desirably at least 50 percent.

The invention is not limited to the above embodiments. The claims follow.

What is claimed is:

1. A polyester compound suitable for hydroclaving, comprising:

(1) polyester;
(2) polysulfone; and
(3) an oligomer which is a polymerization product of
  (i) at least one epoxy-functional (meth)acrylic monomer; and
  (ii) at least one styrene and/or (meth)acrylic monomer,
wherein the polysulfone has a weight of greater than 45 percent of weight of the compound, and
wherein the polyester comprises
  (a) a dicarboxylic acid component comprising:
    i) 70 to 100 mole % of terephthalic acid residues;
    ii) 0 to 30 mole % of aromatic dicarboxylic acid residues having up to 20 carbon atoms other than terephthalic acid residues; and
    iii) 0 to 10 mole % of aliphatic dicarboxylic acid residues having up to 16 carbon atoms; and
  (b) a glycol component comprising:
    i) 1 to 99 mole % of 2,2,4,4-tetramethyl-1,3-cyclobutanediol residues; and
    ii) 1 to 99 mole % of 1,4-cyclohexanedimethanol residues,
wherein the total mole % of the dicarboxylic acid component is 100 mole %, and the total mole % of the glycol component is 100 mole %; and
wherein the inherent viscosity of said polyester is from 0.35 to less than 0.70 dL/g as determined in 60/40 (wt/wt) phenol/tetrachloroethane at a concentration of 0.5 g/100 ml at 25° C.; and
wherein said polyester has a Tg from 110 to 200° C.

2. The compound of claim 1,
wherein the polysulfone has a weight of at least 50 percent of weight of the compound and
wherein the polysulfone has a tensile strength at yield at 23° C. of 70-76 MPa, an elongation at break of 10-80%, a tensile modulus at 23° C. of 1.5-2.7 GPa, a long term service temperature range of 150° C.-180° C., and a heat deflection temperature at 1.8 MPa of 160° C.-174° C.

3. The compound of claim 1, wherein
the polysulfone has a weight of at least 60 percent of weight of the compound and a repeating unit of

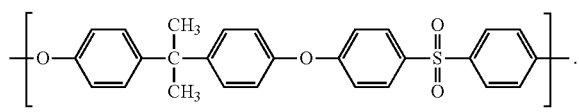

4. The compound of claim 1, wherein the oligomer has an epoxy equivalent weight of from about 180 to about 2800, a number-average epoxy functionality (Efn) value of less than about 30, a weight-average epoxy functionality (Efw) value of up to about 140, and a number-average molecular weight (Mn) value of less than 6000.

5. The compound of claim 4, wherein the oligomer has a polydispersity index of from about 1.5 to about 5.

6. The compound of claim 4, wherein the oligomer has a formula of

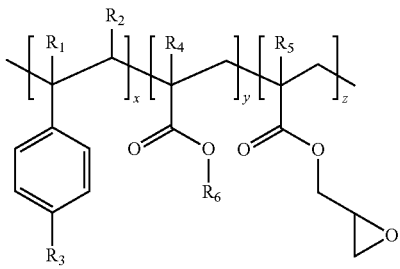

wherein $R_1$-$R_5$ is H, $CH_3$, a higher alkyl group having from 2 to 10 carbon atoms, or combinations thereof; and $R_6$ is an alkyl group; and wherein x, y, and z each is between 1 and 20.

7. The compound of claim 1, wherein the compound further comprises optional additives selected from the group consisting of adhesion promoters; biocides; anti-fogging agents; anti-static agents; bonding, blowing and foaming agents; dispersants; fillers and extenders; fire and flame retardants and smoke suppressants; initiators; lubricants; micas; pigments, colorants and dyes; plasticizers; processing aids; release agents; silanes, titanates and zirconates; slip and anti-blocking agents; stabilizers; stearates; ultraviolet light absorbers; viscosity regulators; waxes; or combinations of them.

8. A plastic article molded from claim 1.

9. The plastic article according to claim 8, wherein the article endures successful repetitious hydroclaving of 135° C. temperature and 248 kPa of steam pressure for at least 18 minutes.

10. The plastic article of claim 9, wherein the article is used in the medical industry and requires steam-based sterilization between each use.

11. The plastic article of claim 8,
wherein the polysulfone has a tensile strength at yield at 23° C. of 70-76 MPa, an elongation at break of 10-80%, a tensile modulus at 23° C. of 1.5-2.7 GPa, a long term service temperature range of 150° C.-180° C., and a heat deflection temperature at 1.8 MPa of 160° C.-174° C.

12. The plastic article of claim 8,
wherein the oligomer
has an epoxy equivalent weight of from about 180 to about 2800, a number-average epoxy functionality (Efn) value of less than about 30, a weight-average epoxy functionality (Efw) value of up to about 140, and a number-average molecular weight (Mn) value of less than 6000.

13. A method of hydroclaving the plastic article of claim 8, comprising the steps of:
(a) heating a hydroclave chamber containing the plastic article to a temperature of 135° C.;
(b) maintaining the temperature of 135° C. at a steam pressure of at least 248 kPa; and
(c) cooling the chamber.

14. The method of claim 13, wherein the plastic article endures successful repetitious hydroclaving of at least 35 cycles without deformation or stickiness.

* * * * *